United States Patent [19]

Borgman

[11] Patent Number: 4,837,378

[45] Date of Patent: Jun. 6, 1989

[54] TOPICAL METRONIDAZOLE FORMULATIONS AND THERAPEUTIC USES THEREOF

[75] Inventor: Robert J. Borgman, Mundelein, Ill.

[73] Assignee: Curatek Pharmaceuticals, Inc., Elk Grove Village, Ill.

[21] Appl. No.: 144,252

[22] Filed: Jan. 15, 1988

Related U.S. Application Data

[63] Continuation-in-part of Ser. No. 819,066, Jan. 15, 1986, abandoned.

[51] Int. Cl.$^4$ .............................................. A61K 31/78
[52] U.S. Cl. ...................................... 424/81; 514/398; 514/859; 514/864
[58] Field of Search ........................... 424/81; 514/398

[56] References Cited

U.S. PATENT DOCUMENTS

| | | | |
|---|---|---|---|
| 2,944,061 | 7/1960 | Jacob | 548/338 |
| 3,883,661 | 5/1975 | Young | 514/859 X |
| 4,491,588 | 1/1985 | Rosenburg et al. | 514/398 X |

OTHER PUBLICATIONS

Chemical Abstracts 103:200872t, Fabre et al (1985).

*Primary Examiner*—Leonard Schenkman
*Attorney, Agent, or Firm*—Dressler, Goldsmith, Shore, Sutker & Milnamow, Ltd.

[57] ABSTRACT

Topical aqueous single-phase compositions containing metronidazole are disclosed. The compositions have improved specific activity and are substantially non-comedogenic, non-irritating and non-skin-drying. These aqueous topical compositions are particularly useful for treating rosacea and other acneform dermatological conditions, and certain forms of dermatitis.

17 Claims, 4 Drawing Sheets

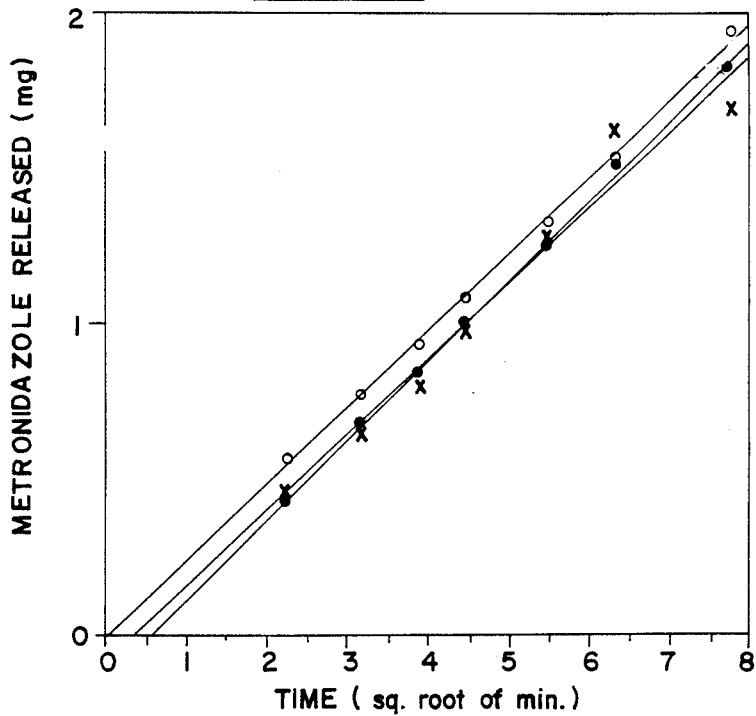
FIG_5_
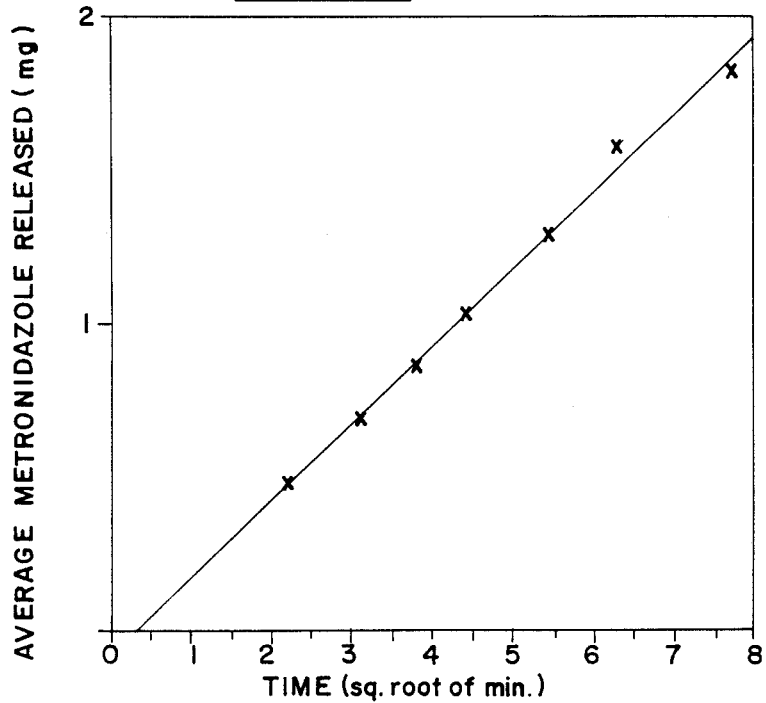
FIG_6_

TOPICAL METRONIDAZOLE FORMULATIONS AND THERAPEUTIC USES THEREOF

CROSS-REFERENCE TO RELATED APPLICATION

This application is a continuation-in-part of copending application U.S. Ser. No. 819,066, filed on Jan. 15, 1986, now abandoned.

TECHNICAL FIELD

This invention relates to novel topical compositions containing metronidazole and methods of treating skin disorders using the same.

BACKGROUND OF THE INVENTION

Metronidazole, 1-(2-hydroxyethyl)-2-methyl-5-nitroimidazole, is a drug known to be effective in treating a variety of disorders. For example, the drug has direct trichomonacidal and amebacidal activity against *Trichomonas vaginalis* and *Entamoeba histolytica*, and is useful in combatting infections caused by those microbial parasites. Metronidazole has also been reported to be effective (via both oral and topical application) in treating skin disorders such as rosacea, ulcers infected with anaerobic bacteria, including decubitus ulcers (bed or pressure sores), venous ulcers, and diabetic foot ulcers, and other anaerobic infections such as post operative sepsis. There have also been reports that metronidazole is effective against perioral dermatitis.

Although oral administration of the drug has been employed for the treatment of certain disorders, long-term oral administration of the drug in cases o chronic disorders such as rosacea may be associated with certain unwanted side effects, and subjects all organ systems needlessly to high drug concentrations. Well-known problems associated with systemic antibiotic therapy include gastro-intestinal intolerance and vaginitis. Thus, topical compositions are generally preferred for dermatological applications. See, for example, "Practical Advice Offered On Rosacea", *Dermatology News*, (April, 1985).

When formulating topical compositions for application to diseased skin, different aspects, such as thermodynamic activity of the drug in the base material vehicle, i.e., the affinity of drug to the vehicle, the release rate of the drug from the vehicle, the type and status of the skin, and the sensitization and irritation potential of components, are factors that can affect the therapeutic effectiveness of topical dermatological preparations. In the case of non-diseased skin with its intact stratum corneum, cell membrane-controlled penetration of the drug occurs. Therefore, a high thermodynamic activity of the drug in the vehicle is desirable, i.e., the drug has a low affinity to the vehicle, and therefore has a high rate of cell membrane penetration to promote transfer of the drug across the epidermal cell membranes. With diseased skin, the release rate of the drug from the vehicle generally is rate-determining for penetration into a patient's cells. Therefore, vehicles which dissolve the drug and have a low diffusional resistance are preferred. In general, drug concentration in the vehicle, and thus the degree of saturation, is considered to be a key formulation factor when optimizing topical delivery for maximum bioavailability.

Rosacea, formerly called *Acne rosacea*, is a chronic skin disease primarily affecting adults, with recurring symptoms that include erythema, papules, pustules, rhinophyma, and telangiectses, primarily in the region of the nose, cheeks, and forehead. In rosacea, other acneform conditions, and certain types of dermatitis, topical treatment compositions are usually applied to both unafflicted and diseased areas. It is therefore desirable that a treatment have a mitigating effect on the diseased tissue and a prophylactic effect to prevent extension of involvement to the unafflicted tissue. Therefore, the preferred vehicles, and hence compositions, to obtain these desirable effects should contain metronidazole in a high thermodynamic activity and with a fast rate of release from the vehicle. Aqueous compositions of metronidazole would appear to meet the above criteria. However, the low solubility of metronidazole in water and several other solvents inhibits the preparation of an aqueous compositions. This has resulted in the development of oil-based, rather than aqueous, metronidazole compositions.

These current topical compositions generally are creams (oil in water emulsions) or ointments (petroleum jelly based compositions) with metronidazole being dissolved in the oil phase. The oils, certain surfactants and emulsifiers, and/or other ingredients utilized in the compositions have been found to be comedogenic, acnegenic, and/or irritating to the skin. See Fulton et al., *Amer. Acad. of Dermatology* 10(1):96–105, (Jan. 1984). Patients treated with such compositions therefore often experience skin problems which include irritation, uncomfortable drying of the skin, and "stinging" or "burning" sensations. In addition, the drug is generally dissolved or dispersed in the oil phase of such preparations, which reduces the specific activity of the drug due to inhibition of drug transfer across the cell membrane. See "Treatment Of Rosacea With 1% Metronidazole Cream. A Double-Blind Study", Nielsen, P., *British J. of Dermatology* 108:327–332 (1983).

Thus, a need remains for metronidazole-containing dermatological preparations suitable for topical use which avoid the problems of current compositions. Such dermatological preparations would be useful for treating skin disorders such as rosacea and certain types of dermatitis, including perioral dermatitis. The present invention provides such preparations.

SUMMARY OF THE INVENTION

In accordance with the present invention, an aqueous gel composition for topical application comprises (a) a therapeutically effective amount of metronidazole, (b) a water-dispersible polycarboxylated vinyl polymer in an amount effective to gel said composition, and (c) an aqueous solvent for the metronidazole. Such compositions are single-phase aqueous gels that provide a relatively high specific activity of metronidazole as compared to prior art oil-based compositions and provide increased bioavailability of the metronidazole. The present compositions are constituted by substantially non-comedogenic, non-irritating ingredients and thus avoid problems associated with the use of prior art formulations in the treatment of skin diseases.

The gel-form compositions of the present invention minimize "pooling" and "running" of the contained medication, e.g., pooling into facial creases, which sometimes occurs with dermatological cream preparations. The resulting local excesses of the creams may contribute to problematic erythema or stinging. The gel-form compositions of the present invention afford more control in application, and better maintenance of a uniform distribution of the drug over the area to be treated, than would generally be expected if the drug were applied as a cream or in an aqueous solution.

The gel advantageously functions as a "sustained delivery" system for the metronidazole, in which the drug continuously is delivered to the cells at, or slightly above, a minimum therapeutically effective level which is sustained over a period of time. This mode of drug release from the vehicle is preferred over vehicles which release the drug at levels much higher than the necessary therapeutic level shortly after application to the skin, followed by a sharp decrease to a level which is not therapeutically effective. The aqueous gel compositions of the present invention function as sustained delivery systems, whereas prior art formulations generally do not provide sustained drug delivery at a relatively constant therapeutically effective level over a period of time.

In one aspect, the present invention therefore provides a method for the prophylactic or therapeutic treatment of humans afflicted with such skin disorders as rosacea, other acneform conditions, e.g., acne vulgaris, steroid acne, acne conglobata, or nodulocystic acne, or certain types of dermatitis, e.g., perioral dermatitis or seborrheic dermatitis.

Numerous other advantages and features of the present invention will become readily apparent from the following description of the preferred embodiments of the invention, the accompanying examples, the drawings and the appended claims.

BRIEF DESCRIPTION OF THE DRAWINGS

In the FIGS. forming a part of the disclosure;

FIG. 5 is a graph illustrating the in-vitro release of metronidazole from a cream composition (1.0 wt-% metronidazole; pH about 3.2) over a 60-minute time period. Data points for Trial One are designated by (o), for Trial Two by (•) and for Trial Three by (x);

FIG. 6 is a graph illustrating the average release of metronidazole for the tree trials shown in FIG. 5;

DESCRIPTION OF PREFERRED EMBODIMENTS

Figure 1:
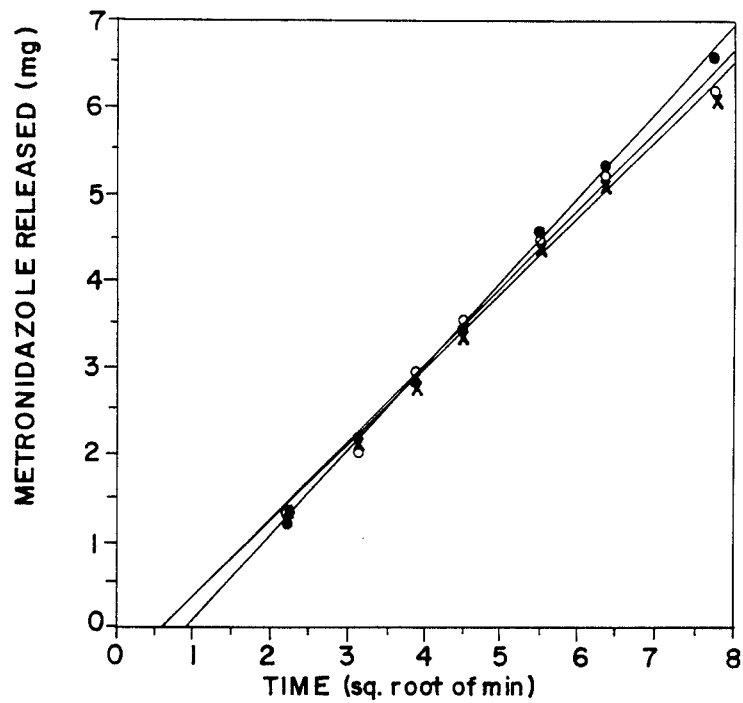
FIG. 1 is a graph illustrating the in-vitro release of metronidazole from a gel composition (0.75 wt-% metronidazole; contains propylene glycol; pH about 5.8) over a 60-minute time period. Data points for Trial One are designated by (o), for Trail Two (•) and for Trial Three by (x)

While this invention is susceptible to embodiment in many different forms, there are shown in the drawings and will be described in detail, preferred embodiments of the invention. It should be understood, however, that the present disclosure is to be considered as an exemplification of the principles of this invention and is not intended to limit the invention to the embodiments illustrated.

The drug 1-(2-hydroxyethyl)-2-methyl-5-nitroimidazole and various derivatives thereof are described in U.S. Pat. No. 2,944,061, to Jacob et al., incorporated herein by reference.

The term "metronidazole" as used in this specification and claims is meant to include not only 1-(2-hydroxyethyl)-2-methyl-5-nitroimidazole, but also those analogs and derivatives of metronidazole which are solubilized in the gel compositions described herein and which have therapeutic activity when topically applied.

Substantially oil-free, aqueous compositions of metronidazole, in which the drug is solubilized in a single-phase aqueous gel, are disclosed. The overall advantages of such aqueous compositions in treating skin disorders have been discussed above, and are presented in greater detail herein below.

Metronidazole is employed in the compositions in a therapeutically effective amount. The actual concentration of metronidazole may vary, depending on the nature and degree of the disorders being treated, and whether the drug is being administered for therapeutic or prophylatic purposes. The compositions advantageously comprise at least about 0.1 wt-% metronidazole, based on the total weight of the composition. Preferably metronidazole is present in an amount of about 0.25% to about 1.0%, and more preferably about 0.75% by weight, based on the total weight of the composition.

In the compositions of the present invention, metronidazole is dissolved in an aqueous solution of a high molecular weight polycarboxylated vinyl polymer. The polymer imparts a desirable viscous, gelled consistency to the composition when mixed with metronidazole and water. The gel compositions contain at least about 95% by weight water, based on the total weight of the composition, and have the requisite degree of metronidazole concentration, and hence thermodynamic activity, for effective topical delivery and bioavailability of metronidazole. The gel compositions of the present invention also have the requisite therapeutic activities as previously described.

The gel-forming polymer useful in compounding the present composition may be any suitable polymer which is hydrophilic and water-dispersible, has free carboxylic groups and relatively high base binding capacity, and forms a gel of substantially uniform consistency when neutralized with a base. Preferred polymers for use in the compositions of the invention are water-dispersible polycarboxylated vinyl polymers. Polyacrylic acid polymers are particularly preferred for the present purposes. The molecular weight of the polymer is desirably in the range of about 1,250,000 and about 4,000,000. Suitable polyacrylic acid polymers include, but are not limited to, polyacrylic acid polymers lightly crosslinked with a polyalkenyl polyether such as those commercially available from B.F. Goodrich, Cincinatti, OH, under the trademarks Carbopol 934, 940, and 941.

Carbopol 940 ® is a particularly preferred polymer for use in practicing this invention.

The polymer is present in an amount sufficient to cause gelling of the composition and impart the desired viscous consistency to the topical formulation. The metronidazole compositions advantageously comprise about 0.2% to about 7.0% by weight of the polymer, preferably about 0.5% to about 1.5%, and most preferably about 0.6% by weight of the polymer based on the total weight of the composition.

Aqueous solutions of these polymers form gels when neutralized with a base. Water-soluble bases which have been used to promote gelling of polymers such as Carbopols$^{TM}$ include inorganic bases such as an aqueous solution of ammonia, NaOH, and organic amines, e.g., alkylamines such as methylamine and ethylamine, dialkylamines, trialkylamines, alkanolamines, dialkanolamines, and the like. The effective component of the compositions of the present invention, metronidazole, is sufficiently basic to partially neutralize the acidic polymer in aqueous solution to the desired degree and to promote gelling.

Optionally, the composition may further include a "penetration enhancer", i.e., an agent that promotes penetration of the active drug into the patient's skin or tissues. Such penetration enhancers include but are not limited to, dimethyl sulfoxide (DMSO) and propylene glycol, with the latter being preferred. The composition advantageously includes about 1.0% to about 50%, preferably about 2% to about 5%, and more preferably about 3% by weight of said penetration enhancer, based on the total weight of the composition.

Preservatives optionally may be incorporated into the compositions in an amount effective for inhibiting growth of microbes such as yeast and molds in the composition during storage. Any conventional preservatives may be used, with parabens being preferred. A mixture of methyl paraben and propyl paraben has been found particularly effective as a preservative. Most preferably, the composition comprises about 0.08% by weight of methyl paraben and about 0.02% by weight of propyl paraben based on the total weight of the composition.

Ethylenediaminetetraacetic acid (EDTA) or one of its salts is commonly added to dermatological preparations, and may optionally be incorporated into the compositions of the present invention. EDTA chelates certain metals that may be present in the formulation, which is useful because some patients have adverse reactions to preparations containing metal impurities. The EDTA will also inhibit undesirable "browning" of the composition which may occur over time in compositions having a low pH value, e.g., a pH value of about 3.5 to about 5.4. Advantageously, the formulation of the invention optionally further includes from about 0.01% to about 0.1%, preferably about 0.5% by weight of EDTA based on the total weight of the composition.

The final pH value of the formulations of the invention may vary within a physiologically compatible range. Advantageously, the final pH value is a physiologically compatible, i.e., not harmful to biological tissue, acidic pH value. The pH value is preferably between about 3 and about 6.9, and most preferably between about 4 and 5. Any suitable method of adjusting the pH value of aqueous solutions may be used. Advantageously, sodium hydroxide (NaOH) is added to the composition to bring the final pH value to the desired level. Gel compositions of the invention are more viscous at pH values that approach neutrality than at the more acidic pH values within the preferred range, i.e., viscosity increases as the polymer in the gel is neutralized to a greater degree, e.g., with NaOH.

The ingredients listed above may be combined in any order and manner that produces a composition comprising metronidazole dissolved in, and evenly dispersed throughout, a one-phase aqueous gel of the desired consistency and pH value. One suitable method of preparing compositions of the invention involves preparation of an aqueous solution of the polymer, which will be called "Part A". Advantageously, this solution comprises the polymer in distilled water. A "Part B" is prepared comprising metronidazole. Mixing of Parts A and B results in gelling of the composition. The optional penetration enhancer and preservative(s) are preferably included in Part B. If EDTA is to be added to the formulation, it is preferably included in Part A. The pH value may then be adjusted to the desired level, e.g., by addition of NaOH.

The resulting homogeneous gels possess the advantageous properties described above, including utliziing non-comedogenic, non-acneogenic, and non-irritating ingredients; higher specific activity of metronidazole due to increased diffusion across membranes and release from the vehicle which results in greater therapeutic effectiveness using smaller amounts of metronidazole; and a desirable consistency that prevents undesired pooling and spreading of metronidazole. High concentrations of skin-drying ingredients (e.g. alcohols and acetone), which are found in some dermatological preparations to promote drug solubility, are also avoided. Such ingredients at high concentration may excessively dry the patient's skin, causing undesirable flaking and discomfort.

The therapeutic effectiveness of the metronidazole compositions of the present invention is demonstrated in the following examples. These examples are meant to illustrate the invention rather than to limit its scope. Variations in the compositions which do not adversely affect the effectiveness of metronidazole will be evident to one skilled in the art, and are within the scope of this invention. For example, additional ingredients such as coloring agents, sunscreens, and the like may be included in the compositions as long as the resulting composition retains the desirable properties, e.g., non-comedogenicity, high specific activity, and the like, described above.

EXAMPLE I

A 30 kilogram batch of a composition of the present invention was prepared as follows. 180 Grams of Carbopol 940 ® (0.6% by weight of the final weight of the composition) was dissolved in 16.5 liters of distilled water containing 15 grams of ethylenediaminetetraacetic acid (EDTA) disodium dihydrate. Sufficient amount of 10 wt-% sodium hydroxide (NaOH) solution was added to bring the pH value to about 5. This aqueous polymer solution was called "Part A". "Part B" was prepared by mixing 900 grams of propylene glycol (3% by weight of the final weight of the composition), 24 grams of methyl paraben (0.08% by weight of the final weight of the composition) and 6.0 grams of propyl paraben (0.02% by weight of the final weight of the composition). The mixture was added to 225 grams of metronidazole dispersed in 11.4 liters of distilled water maintained at 50° C. Parts A and B were then mixed thoroughly and gelling of the composition resulted. A cold aqueous solution of NaOH was then used to adjust the final pH value to 5.25. Distilled water was then added to give the desired 30 kilogram final weight. The NaOH and water were thoroughly mixed into the viscous gel.

A random, double blind, placebo controlled clinical trail was conducted to demonstrate the positive clinical efficacy of the aqueous metronidazole-containing gel composition prepared in Example I in treating rosacea. The study included patients who had received no prior treatment for resacea, as well as patients who had been treated by conventional methods. Patients discontinued treatment, if any, at least 21 days prior to the start of the study. Each patient received metronidazole in the gel composition on one side of the face and the gel composition (placebo control) without metronidazole on the other side of the face. Therefore, in this study, each patient served as their own control.

The effectiveness of the treatment was rated, at the time points indicated in the TABLES below, in six different categories, namely, reduction in inflammatory lesions (papules and pustules), erythema, stinging, burning, itching, and dryness. The data are shown in the Tables below.

Table I-A shows the percent reduction in inflammatory lesions (papules and pustules) form baseline values for active (i.e., metronidazole-treated) and placebo-treated sides. Inflammatory lesions were progressively reduced from 46.7% to 59.9% for active-treated sides while placebo-treated sides reflected an exacerbation. There was an 82.6% difference in inflammatory lesions at the end of drug treatment on the metronidazole versus placebo-treated sides.

Table I-B shows mean erythema values for active and placebo-treated sides. Statistically significant differences were found at visits 2, 3, 4 and 5 for the active sides and at visits 3 and 4 for the placebo sides, when compared to baseline values. Active and placebo-side values were significantly different from each other at visits 3, 4 and 5. A concomitant improvement in reduction of erythema was seen at the same time point on the treated side and on the placebo side.

Tables II-A, II-B, II-C, and II-D show an unexpected but dramatic improvement in local tolerance data. This data represents the patient's subjective assessments of stinging, buring, itching and dryness one each side of their faces before and during drug or placebo treatment. The data shows that there was a dramatic (highly statistically significant) improvement in the patient's perceptions of these attendant complications of the disease. Since both sides improved to the same degree, i.e., no statistically significant difference can be found, the improvement apparently comes from the gel composition per se.

Table II-A shows mean stinging scores for active and placebo-treated sides. Statistically significant differences were found at visits 3, 4 and 5 for both the active and placebo sides, when compared to baseline values. Active and placebo-side values were not significantly different from one another.

Table II-B shows mean burning scores for active and placebo-treated sides. Statistically significant differences were found at all visits (2, 3, 4, 5) for both the active and placebo sides, when compared to baseline values. Active and placebo-side values were not significantly different from one another.

Table II-C shows mean itching scores for active and placebo-treated sides. Statistically significant differences were found at all visits (2, 3, 4, 5) for both the active and placebo sides, when compared to baseline values. Active and placebo-side values were not significantly different from one another.

Table II-D shows means dryness scores for active and placebo-treated sides. Statistically significant differences were found at visits 3, 4 and 5 for active sides and at visits 4 and 5 for placebo sides, when compared to baseline values. Active and placebo-side values were not significantly different from one another.

This data confirms the effectiveness of metronidazole in the gel composition for treatment of rosacea and also demonstrates the unique therapeutic effects of the gel composition.

TABLE I-A

Inflammatory Lesions
(Efficacy Data From 20 Subjects)

| | On Drug | | | Off Drug |
|---|---|---|---|---|
| | Visit 2 Weeks 3–5 | Visit 3 Weeks 6–8 | Visit 4 Weeks 9–11 | Visit 5 Weeks 12–17 |
| Active (Percent Reduction from Baseline) | 46.7 | 55.1 | 59.9 | 41.6 |
| Placebo (Percent Reduction from Baseline) | −22.5 | −4.2 | −22.7 | −46.8 |
| Difference (Active-Placebo Percent Difference) | 69.2 | 59.3 | 82.6 | 88.4 |

TABLE I-B

Erythema
(Efficacy Data From 20 Subjects)

| | | On Drug | | | Off Drug |
|---|---|---|---|---|---|
| | Visit 1 Baseline | Visit 2 Weeks 3–5 | Visit 3 Weeks 6–8 | Visit 4 Weeks 9–11 | Visit 5 Weeks 12–17 |
| Active (Mean Values) | 2.10 | 1.55**** | 1.05*** | 1.05*** | 1.15*** |
| Placebo (Mean Values) | 2.10 | 1.90 | 1.55*** | 1.55*** | 1.70 |
| 3 = Severe | | | | | |
| 2 = Moderate | | | | | |
| 1 = Mild | | | | | |
| 0 = Absent | | | | | |
| Active Versus Placebo Significant Differences (p values) | None | None | p < 0.02 | p < 0.02 | p < 0.02 |

***p < 0.01 compared to baseline values.

TABLE II-A

Stinging
(Local Tolerance Data from 20 Subjects)

| | | On Drug | | | Off Drug |
|---|---|---|---|---|---|
| | Visit 1 Baseline | Visit 2 Weeks 3–5 | Visit 3 Weeks 6–8 | Visit 4 Weeks 9–11 | Visit 5 Weeks 12–17 |
| Active (Mean Values) | 0.70 | 0.25 | 0.15** | 0.00*** | 0.00*** |
| Placebo | 0.65 | 0.30 | 0.15* | 0.20* | 0.05*** |

TABLE II-A-continued

Stinging
(Local Tolerance Data from 20 Subjects)

|  | On Drug | | | Off Drug |
| --- | --- | --- | --- | --- |
|  | Visit 2 | Visit 3 | Visit 4 | Visit 5 |
| Visit 1 | Weeks | Weeks | Weeks | Weeks |
| Baseline | 3–5 | 6–8 | 9–11 | 12–17 |
| (Mean Values) | | | | |
| 3 = Severe | | | | |
| 2 = Moderate | | | | |
| 1 = Mild | | | | |
| 0 = Absent | | | | |
| Active Versus Placebo Significant Differences (p values) | None | None | None | None | None |

*p < 0.05 compared to baseline values.
**p < 0.02 compared to baseline values
***p < 0.01 compared to baseline values

TABLE II-B

Burning
(Local Tolerance Data from 20 Subjects)

|  | On Drug | | | Off Drug |
| --- | --- | --- | --- | --- |
|  | Visit 2 | Visit 3 | Visit 4 | Visit 5 |
| Visit 1 | Weeks | Weeks | Weeks | Weeks |
| Baseline | 3–5 | 6–8 | 9–11 | 12–17 |
| Active (Mean Values) | 1.25 | 0.30** | 0.10*** | 0.05*** | 0.05*** |
| Placebo (Mean Values) | 1.05 | 0.30*** | 0.05*** | 0.10*** | 0.05*** |
| 3 = Severe | | | | |
| 2 = Moderate | | | | |
| 1 = Mild | | | | |
| 0 = Absent | | | | |
| Active Versus Placebo Significant Differences (p values) | None | None | None | None | None |

**p < 0.02 compared to baseline values.
***p < 0.01 compared to baseline values

TABLE II-C

Itching
(Local Tolerance Data from 20 Subjects)

|  | On Drug | | | Off Drug |
| --- | --- | --- | --- | --- |
|  | Visit 2 | Visit 3 | Visit 4 | Visit 5 |
| Visit 1 | Weeks | Weeks | Weeks | Weeks |
| Baseline | 3–5 | 6–8 | 9–11 | 12–17 |
| Active (Mean Values) | 1.45 | 0.55*** | 0.15*** | 0.20*** | 0.10*** |
| Placebo (Mean Values) | 1.40 | 0.70*** | 0.25*** | 0.20*** | 0.15*** |
| 3 = Severe | | | | |
| 2 = Moderate | | | | |
| 1 = Mild | | | | |
| 0 = Absent | | | | |
| Active Versus Placebo Significant Differences (p values) | None | None | None | None | None |

***p < 0.01 compared to baseline values

TABLE II-D

Dryness
(Local Tolerance Data from 20 Subjects)

|  | On Drug | | | Off Drug |
| --- | --- | --- | --- | --- |
|  | Visit 2 | Visit 3 | Visit 4 | Visit 5 |
| Visit 1 | Weeks | Weeks | Weeks | Weeks |
| Baseline | 3–5 | 6–8 | 9–11 | 12–17 |
| Active (Mean Values) | 1.45 | 0.85 | 0.50*** | 0.25*** | 0.25*** |
| Placebo (Mean Values) | 1.40 | 0.85 | 0.75 | 0.20*** | 0.45*** |
| 3 = Severe | | | | |
| 2 = Moderate | | | | |
| 1 = Mild | | | | |
| 0 = Absent | | | | |
| Active Versus Placebo Significant Differences (p values) | None | None | None | None | None |

***p < 0.01 compared to baseline values

A study was conducted to determine differences in the in-vitro release characteristics of metronidazole from various topical compositions using the following experimental procedure.

The metronidazole gel or cream was placed into a shallow well about 1 millimeter deep created by a Plexiglass ® template placed on a round 5.2 centimeter Plexiglass ® base. The diameter of the template into which the composition was placed was 3.0 centimeters. The composition was covered by a piece of Spectrapor$^{TM}$ membrane (available from Spectrum Medical Industries, Inc., Los Angeles, CA 90054) having a molecular weight cutoff of between 12,000 and 14,000. The membrane had been soaked in a buffer having a pH value of 5.5 for 24 hours. A second template identical in size to the template forming the well was utilized to hold the membrane in place. The templates were secured by four nylon screws thereby creating a holder. 400 Cubic centimeters of an acetate buffer solution having a pH value of 5.5 was placed in a round bottom dissolution flask (available from Hanson Research Corporation, Northridge, CA 91324) and the temperature of the solution was equilibrated to 32° C. A solid halogenated hydrocarbon polymer-coated stirrer was lowered into a position 2.54 centimeters above the membrane surface. The solution was stirred at 50 RPM. Five cubic centimeter samples were removed at 5, 10, 15, 20, 30, 40, and 60 minutes. The volume of the sample was replaced each time with fresh solution. The samples were analyzed at 319 nanometers on a spectrophotometer (Model 8450A, Hewlett-Packard, Palo Alto, CA 94303).

After absorbance was converted to concentration using a Beer's Law plot, the total milligrams of metronidazole released at each time point was calculated from the following equation:

$$\text{Metronidazole released (mg)} = \frac{[\text{Concentration } (\mu\text{mg/cc})] \times [400 \text{ cc}]}{[1000 \text{ micrograms/milligrams}]}$$

Additional compositions that have been studied are shown in TABLE III, below. These compositions were prepared in substantially the same manner as described in Example I, above.

TABLE III

| Components | Compositions, in wt. % | | |
|---|---|---|---|
| | C1 | C2 | C3 |
| Metronidazole | 0.75 | 0.75 | 1.00 |
| Propylene Glycol | 3.00 | — | — |
| Polyacrylic Acid Polymer[1] | 0.60 | 0.60 | — |
| Methyl Paraben | 0.08 | 0.08 | — |
| Propyl Paraben | 0.02 | 0.02 | — |
| Disodium EDTA | 0.05 | 0.05 | — |
| Cetylane | — | — | 5.00 |
| Cetyl Alcohol | — | — | 15.00 |
| Sodium Lauryl Sulfate | — | — | 1.50 |
| Lactic Acid | — | — | 1.50 |
| Water, q.s. ad | 100.00 | 100.00 | 100.00 |

[1]Carbopol 940 from B. F. Goodrich Company, a commercially available polyacrylic acid polymer having a molecular weight of about 4,000,000.

Figure 2:
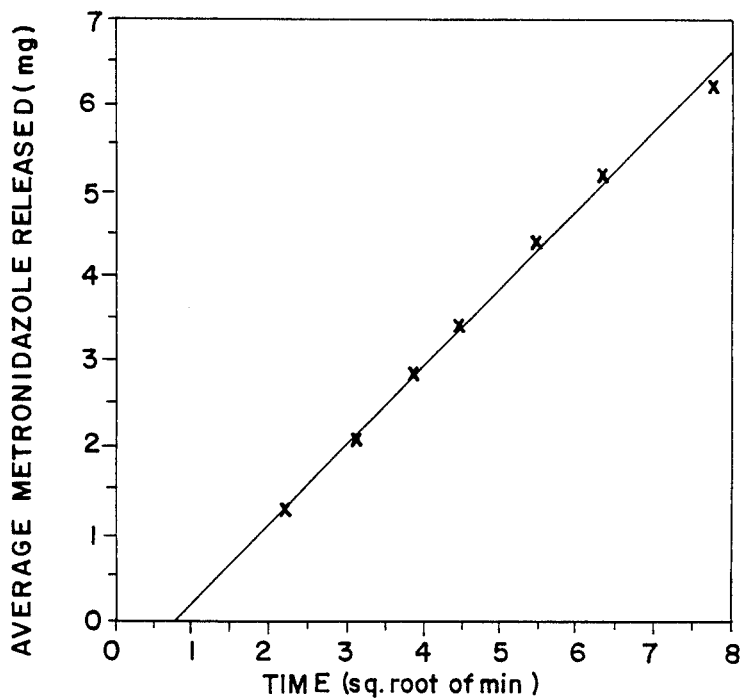
FIG. 2 is a graph illustrating the average release of metronidazole for the three trials shown in FIG. 1.

Data from three trials for the release of metronidazole from C1, a gel composition, (0.75 wt-% metronidazole; pH value about 5.8) are presented in TABLE IV and are plotted in FIG. 1. In FIG. 1, Trial One is denoted by (o), Trial Two by ● and Trial Three by (x). The average data for the three trials is presented in TABLE VII and is plotted in FIG. 2. Traditional linear plots for release of drugs from ointment bases are obtained by plotting amount released vs. the square root of time.

TABLE IV

| | Release of Metronidazole from C1 (mg) | | |
|---|---|---|---|
| Time (Min) | Trial One | Trial Two | Trial Three |
| 0 | 0 | 0 | 0 |
| 5 | 1.37 | 1.26 | 1.33 |
| 10 | 2.09 | 2.14 | 2.14 |
| 15 | 2.96 | 2.86 | 2.86 |
| 20 | 3.54 | 3.47 | 3.44 |
| 30 | 4.50 | 4.54 | 4.38 |
| 40 | 5.19 | 5.34 | 5.10 |
| 60 | 6.16 | 6.53 | 6.09 |

Figure 3:
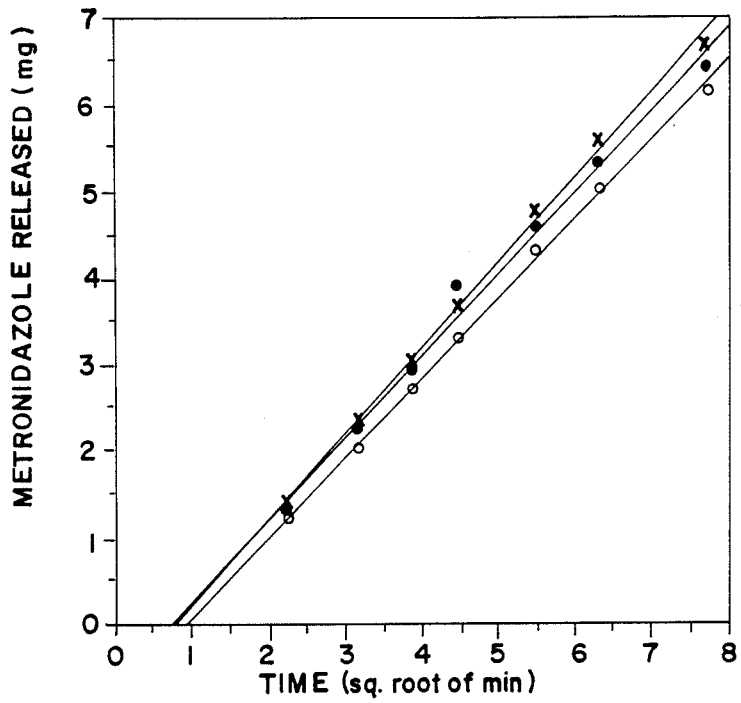
FIG. 3 is a graph illustrating the in-vitro release of metronidazole from another gel composition (0.75 wt-% metronidazole; no propylene glycol; pH about 5.8) over a 60-minute time period. Data points for Trial One are designated by (o), for Trial Two by (•) and for Trail Three by (x)
Figure 4:
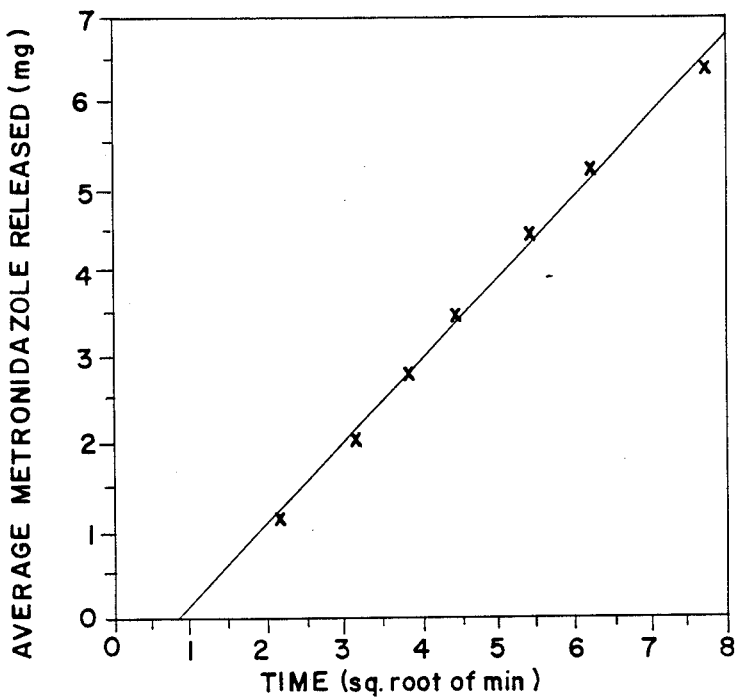
FIG. 4 is a graph illustrating the average release of metronidazole for the three trials shown in FIG. 3.

Data from three trials for the release of metronidazole from C2, another gel composition, (0.75 wt-% metronidazole, without propylene glycol; pH value about 5.8) are presented in TABLE V and are plotted in FIG. 3. In FIG. 3, Trial One is denoted by (o), Trial Two by (●) and Trial Three by (x). The average data for the three trials is presented in TABLE VII and are plotted in FIG. 4. Again, traditional linear plots for release of drugs from ointment bases are obtained by plotting amount released vs. the square root of time.

TABLE V

| | Release of Metronidazole from C2 (mg) | | |
|---|---|---|---|
| Time (Min) | Trial One | Trial Two | Trial Three |
| 0 | 0 | 0 | 0 |
| 5 | 1.21 | 1.27 | 1.39 |
| 10 | 2.02 | 2.18 | 2.29 |
| 15 | 2.70 | 2.95 | 3.04 |
| 20 | 3.29 | 3.89 | 3.67 |
| 30 | 4.30 | 4.62 | 4.75 |
| 40 | 5.02 | 5.32 | 5.57 |
| 60 | 6.15 | 6.41 | 6.69 |

Data from three trials for the release of the metronidazole from C3, a cream composition, (1.0 wt-% metronidazole; pH value about 3.2) are presented in TABLE VI and are plotted in FIG. 5. In FIG. 5, Trial One is denoted by (o), Trial Two by (●) and Trial Three by (x). The average data for the three trials are presented in TABLE VII and are plotted in FIG. 6. Again, traditional linear plots for release of drugs from ointment bases are obtained by plotting amount released vs. the square root of time.

TABLE VI

| | Release of Metronidazole from C3 (mg) | | |
|---|---|---|---|
| Time (Min) | Trial One | Trial Two | Trial Three |
| 0 | 0 | 0 | 0 |
| 5 | 0.56 | 0.42 | 0.46 |
| 10 | 0.78 | 0.67 | 0.66 |
| 15 | 0.94 | 0.85 | 0.82 |
| 20 | 1.09 | 0.98 | — |
| 30 | 1.32 | 1.25 | 1.29 |
| 40 | 1.53 | 1.54 | 1.63 |
| 60 | 1.94 | 1.82 | 1.69 |

TABLE VII

| | Average Release of Metronidazole (mg) | | |
|---|---|---|---|
| Time (Min) | C1 | C2 | C3 |
| 0 | 0 | 0 | 0 |
| 5 | 1.32 ± 0.06 | 1.29 ± 0.09 | 0.48 ± 0.07 |
| 10 | 2.12 ± 0.03 | 2.16 ± 0.14 | 0.70 ± 0.07 |
| 15 | 2.89 ± 0.06 | 2.90 ± 0.18 | 0.87 ± 0.06 |
| 20 | 3.48 ± 0.05 | 3.62 ± 0.30 | 1.04 ± 0.08 |
| 30 | 4.47 ± 0.08 | 4.56 ± 0.23 | 1.29 ± 0.04 |
| 40 | 5.21 ± 0.12 | 5.30 ± 0.28 | 1.57 ± 0.06 |
| 60 | 6.26 ± 0.24 | 6.42 ± 0.27 | 1.82 ± 0.13 |

Figure 7:
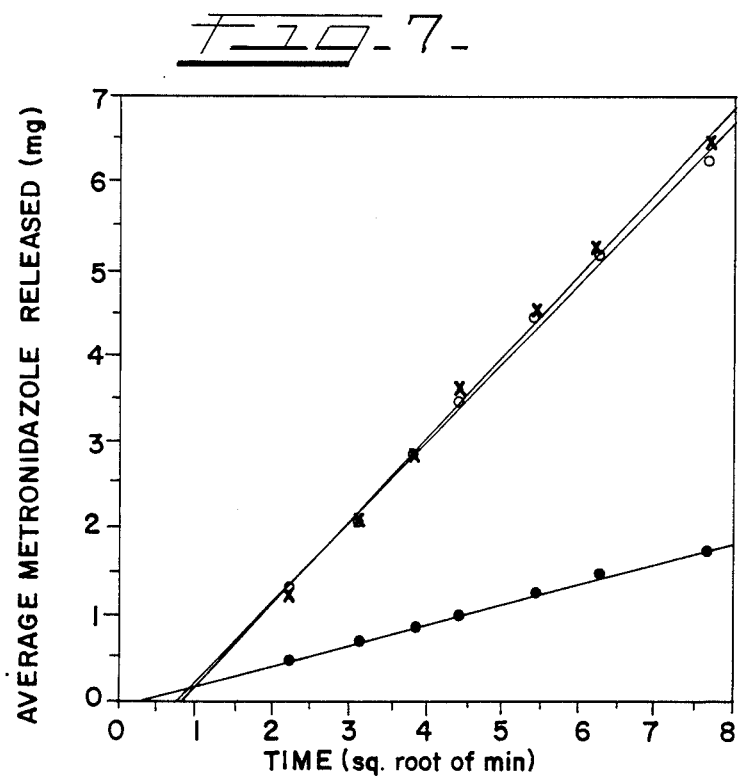
FIG. 7 is a graph illustrating the average in-vitro release of metronidazole over a 60-minute time period. Data points for a gel composition (0.75 wt-% metronidazole containing propylene glycol; pH about 5.8) are designated by (o), for another gel composition (0.75 wt-% metronidazole; no propylene glycol; pH about 5.8) by (x) and for a cream composition (1.0 wt-% metronidazole; pH about 3.2) by(•).

TABLE VIII and FIG. 7 show, for comparison purposes, the average metronidazole released from C1 (o), C2 (x) and C3(●). The large difference in the slopes of the plots indicate that the release rate of the gel compositions, i.e., C1 and C2, is about 3.7 times greater than that from the cream, i.e., C3.

TABLE VIII

| Comparison of the Release Rates (Slopes) of the Three Compositions | |
|---|---|
| Composition | Release Rates (mg/min$^{(1/2)}$) |
| C1 | 0.9166 ± 0.0492 |
| C2 | 0.9465 ± 0.0349 |
| C3 | 0.2505 ± 0.0071 |

The in-vitro release of metronidazole from the gel formulations with or without propylene glycol is either 3.66 or 3.78 times faster, respectively, than that of the metronidazole from the cream formulation C3.

The foregoing specification is intended as illustrative and is not to be taken as limiting. Still other variations within the spirit and the scope of the invention are possible and will readily present themselves to those skilled in the art.

I claim:

1. A dermatological preparation for topical application in the form of an aqueous gel composition comprising:
    a therapeutically effective amount of metronidazole as the sole active ingredient;
    a gelled, hydrophillic and water-dispersible polymer having free carboxylic groups which is a polyacrylic acid polymer having a molecular weight in the range of about 1,250,000 to about 4,000,000 daltons; and
    an aqueous solvent for said metronidazole.

2. The preparation in accordance with claim 1 wherein the concentration of said metronidazole is at least about 0.1 percent by weight based on the total weight of said composition.

3. The preparation in accordance with claim 2 wherein the concentration of said metronidazole present is in the range of about 0.25 precent to about 1.0 percent by weight based on the total weight of said composition.

4. The preparation in accordance with claim 3 wherein the concentration of said metronidazole present is about 0.75 percent by weight based on the total weight of said composition.

5. The preparation in accordance with claim 1 wherein said polymer is present in a range of about 0.2 percent to about 7.0 percent by weight based on the total weight of said composition.

6. The preparation in accordance with claim 5 wherein said polymer is present in a range of about 0.5 percent to about 1.5 percent by weight based on the total weight of said composition.

7. The preparation in accordance with claim 6 wherein said polymer is present in an amount of about 0.6 percent by weight based on the total weight of said composition.

8. The preparation in accordance with claim 1 further including a penetration enhancer.

9. The preparation in accordance with claim 8 wherein said penetration enhancer is propylene glycol present in a range of about 2 percent to about 5 percent by weight based on the total weight of said composition.

10. The preparation in accordance with claim 9 wherein said penetration enhancer is present in an amount of about 3 percent by weight based on the total weight of the composition.

11. The preparation in accordance with claim 1 further including a preservative.

12. The preparation in accordance with claim 11 wherein said preservative comprises at least one paraben.

13. The preparation in accordance with claim 12 wherein said preservative is methyl paraben present in an amount about 0.08 weight percent and propyl paraben present in an amount of about 0.02 weight percent, based on the total weight of said composition.

14. The preparation in accordance with claim 1 further including ethylenediaminetetraacetic acid in a range of about 0.01 percent to about 0.1 percent by weight based on the total weight of said composition.

15. A method for treatment of a human afflicted with a skin disorder which is a member of the group consisting of acne, rosacea, perioral dermatitis and seborrheic dermatitis, said method comprising topically applying to the afflicted skin region a therapeutically effective amount of a dermatological preparation in the form of an aqueous gel composition comprising:
  a therapeutically effective amount of metronidazole as the sole active ingredient;
  a gelled hydrophilic and water-dispersible polymer having free carboxylic groups which is a polyacrylic acid polymer having a molecular weight in the range of about 1,250,000 to about 4,000,000 daltons; and
  an aqueous solvent for said metronidazole.

16. The method of claim 15 wherein said skin disorder is rosacea.

17. The method of claim 15 wherein said skin disorder is acne vulgaris.

* * * * *